US012303346B2

(12) United States Patent
Salah et al.

(10) Patent No.: US 12,303,346 B2
(45) Date of Patent: May 20, 2025

(54) METHOD FOR SIMULATING A DENTAL SITUATION

(71) Applicant: DENTAL MONITORING, Paris (FR)

(72) Inventors: Philippe Salah, Paris (FR); Thomas Pellissard, Paris (FR); Guillaume Ghyselinck, Cantin (FR); Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 0 days.

(21) Appl. No.: 17/259,516

(22) PCT Filed: Jul. 10, 2019

(86) PCT No.: PCT/EP2019/068558
§ 371 (c)(1),
(2) Date: Jan. 11, 2021

(87) PCT Pub. No.: WO2020/011864
PCT Pub. Date: Jan. 16, 2020

(65) Prior Publication Data
US 2021/0267716 A1 Sep. 2, 2021

(30) Foreign Application Priority Data

Jul. 13, 2018 (FR) ...................... 1856498

(51) Int. Cl.
G06T 15/00 (2011.01)
A61C 7/00 (2006.01)
(Continued)

(52) U.S. Cl.
CPC .......... A61C 7/002 (2013.01); A61C 13/0004 (2013.01); G06F 30/27 (2020.01);
(Continued)

(58) Field of Classification Search
CPC ........ G16H 30/20; G16H 50/20; G16H 50/50; G16H 30/40; A61C 7/002; A61C 13/0004; G06F 30/27; G06N 3/08; A61B 1/24
(Continued)

(56) References Cited

U.S. PATENT DOCUMENTS

| 10,660,728 | B2* | 5/2020 | Maraj ................. G06T 19/006 |
| 10,898,298 | B1* | 1/2021 | Raslambekov ........ A61B 5/055 |
| 11,107,218 | B2* | 8/2021 | Salah .................. G06T 7/0014 |
| 11,229,504 | B1* | 1/2022 | Wucher ................ A61C 7/002 |
| 11,321,918 | B2* | 5/2022 | Jørgensen .............. G06T 9/001 |
| 2017/0169492 | A1* | 6/2017 | Reggiardo, III ... G06Q 30/0621 |

(Continued)

FOREIGN PATENT DOCUMENTS

WO 2018069736 A1 4/2018

OTHER PUBLICATIONS

Murata S, Lee C, Tanikawa C, Date S. Towards a fully automated diagnostic system for orthodontic treatment in dentistry. In2017 IEEE 13th international conference on e-science (e-science) Oct. 24, 2017 (pp. 1-8). IEEE.*

(Continued)

Primary Examiner — Phu K Nguyen
(74) Attorney, Agent, or Firm — Ronald M. Kachmarik; Cooper Legal Group LLC

(57) ABSTRACT

A simulating method. The method includes acquiring an image of a dental arch of a patient, called the "original image." The method includes subjecting the original image to a neural network, called the "modification neural network", trained to locally modify the original image in order to obtain a "modified image." The method includes presenting the modified image to the patient.

14 Claims, 2 Drawing Sheets

(51) Int. Cl.

| | |
|---|---|
| *A61C 13/00* | (2006.01) |
| *G06F 30/27* | (2020.01) |
| *G06N 3/08* | (2023.01) |
| *G16H 30/20* | (2018.01) |
| *G16H 30/40* | (2018.01) |
| *G16H 50/20* | (2018.01) |
| *G16H 50/50* | (2018.01) |
| *A61B 1/24* | (2006.01) |

(52) U.S. Cl.
CPC ............... *G06N 3/08* (2013.01); *G16H 30/20* (2018.01); *G16H 30/40* (2018.01); *G16H 50/20* (2018.01); *G16H 50/50* (2018.01); *A61B 1/24* (2013.01)

(58) Field of Classification Search
USPC .......................................................... 345/418
See application file for complete search history.

(56) References Cited

U.S. PATENT DOCUMENTS

| | | |
|---|---|---|
| 2018/0110590 A1 | 4/2018 | Maraj et al. |
| 2018/0168780 A1 | 6/2018 | Kopelman et al. |
| 2018/0174367 A1 | 6/2018 | Marom et al. |
| 2018/0206940 A1* | 7/2018 | Kopelman ............. A61C 7/002 |
| 2020/0405447 A1* | 12/2020 | Salah ..................... A61C 13/34 |

OTHER PUBLICATIONS

Daher et al, 3D Digital Smile Design With a Mobile Phone and Intraoral Optical Scanner; Copendium of Continuing Education in Dentistry, vol. 39, Issue 6, Jun. 2018.*

Giordano V, Koch HA, Mendes CH, Bergamin A, de Souza FS, do Amaral NP. WhatsApp Messenger is useful and reproducible in the assessment of tibial plateau fractures: inter-and intra-observer agreement study. International journal of medical informatics. Feb. 1, 2015;84(2):141-8.*

Ivanov, Pavel. "Three-dimensional Scanning of Objects Using a Mobile Phone: Photogrammetry Silhouette Technique." (2017).*

Fogel AL, Kvedar JC. Artificial intelligence powers digital medicine. NPJ digital medicine. Mar. 14, 2018;1(1):5.*

Loh E. Medicine and the rise of the robots: a qualitative review of recent advances of artificial intelligence in health. BMJ leader. Jun. 1, 2018:leader-2018.*

Abhijeet K, Mody E, Jei JB, John P, Krishnan M, Muthukumar B. Mobile Phone Assisted 3D Extra Oral Scanner for Acquiring Dental Digital Models—An Innovative Approach. Journal of Evolution of Medical and Dental Sciences. Jun. 7, 2021;10(23):1815-9.*

International Search Report corresponding to International Application No. PCT/EP2019/068558 dated Oct. 9, 2019, 7 pages.

Karim Armanious, et al., "MedGAN: Medical Image Translation using GANs", Jun. 17, 2018, https://arxiv.org/pdf/1806.06397.pdf.

Fernandez Kelwin, et al., Teeth/Palate and Interdental Segmentation Using Artificial Neural Networks, International Conference on Computer Analysis of Images and Patterns. CAIP 2017: Computer Analysis of Images and Patterns; [Lecture Notes in Computer Science; Lect.Notes Computer] Springer, Berlin, Heidelberg, pp. 175-185, Sep. 17, 2012.

Anonymous, "Artificial neural network", Wikipedia, Jul. 5, 2018, https://en.wikipedia.org/w/index.php?title=Artificial_neural_network&oldid=849005879.

Chinese Office Action from Corresponding Chinese Application No. 201980046736.3, dated Aug. 30, 2024.

* cited by examiner a) acquiring an image of a dental arch of a patient, called the "bare image"
b) subjecting the bare image to a neural network trained to represent an orthodontic appliance in images, so as to obtain an image representing said dental arch and the orthodontic appliance borne by said arch, called the "completed image"
c) presenting the completed image to the patient.
Fig. 1
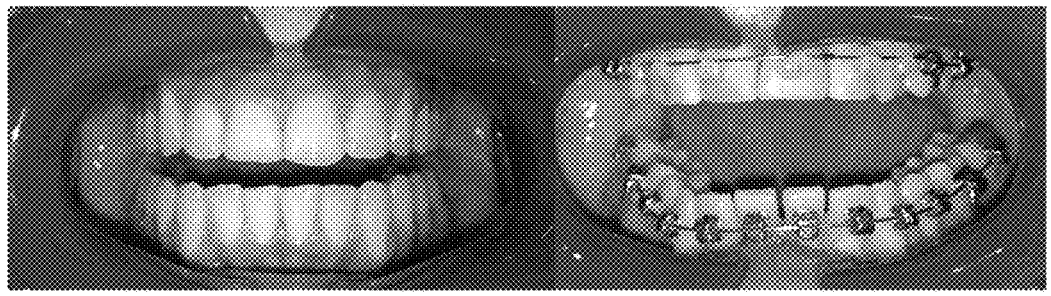
Fig. 2A  Fig. 2B
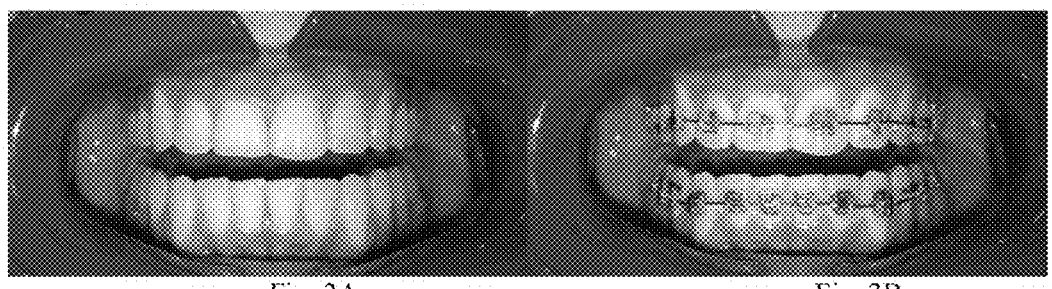
Fig. 3A  Fig. 3B
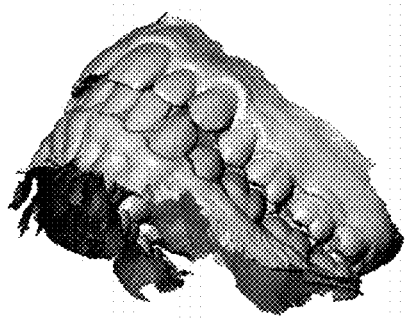 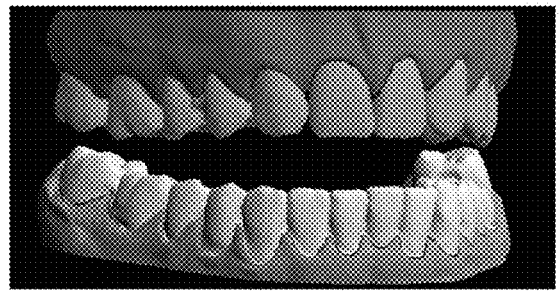
Fig. 4  Fig. 5

12,303,346 B2

METHOD FOR SIMULATING A DENTAL SITUATION

TECHNICAL FIELD

The present invention relates to a simulating method allowing a hyperrealistic dental view simulating what an orthodontic appliance will look like when worn to be generated.

PRIOR ART

The adherence of a patient to an orthodontic treatment is important to the success of this treatment. In particular, wearing an orthodontic appliance modifies the appearance of the patient, this possibly discouraging them from pursuing the treatment.

There is therefore a need for a method that will allow this adherence to be improved.

One aim of the invention is to at least partially meet this need.

SUMMARY OF THE INVENTION

The invention provides a simulating method comprising the following steps:
a) acquiring an image containing a dental arch of a patient, called the "original image";
b) subjecting the original image to a neural network, called the "modification neural network", trained to locally modify the original image in order to obtain a "modified image";
c) preferably, presenting the modified image to the patient.

As will be seen in more detail in the remainder of the description, such a neural network is capable of converting the original image in a surprisingly realistic manner. A method according to the invention thus allows a representation of an orthodontic appliance to be incorporated into the original image, or an orthodontic appliance contained in the original image to be modified, or an orthodontic appliance contained in the original image to be deleted. The patient may thus benefit from a simulation that allows them to properly measure the visual impact of wearing the orthodontic appliance or of a change in orthodontic appliance.

The adherence of the patient to the orthodontic treatment is reinforced thereby.

A method according to the invention is noteworthy in that the neural network is trained to create a modified image from the original image delivered thereto. This method is therefore quite different from a method in which, for example, an element, for example a representation of an existing orthodontic appliance, is added to an image. Specifically, to incorporate a representation of an orthodontic appliance into the original image, the neural network creates this representation. This representation is therefore not the reproduction of an actual orthodontic appliance or of a three-dimensional model of an actual orthodontic appliance, but is generated by the neural network in an artificial way, at the same time as the rest of the image.

Surprisingly, the representation of the orthodontic appliance is very realistic and provides a good simulation for the patient to be obtained, as shown in FIG. 3B. In particular, the training of the neural network teaches it how to represent the orthodontic appliance in the context of the original image, with the corresponding contrast, sharpness, shadows and reflections. The simulation is therefore much more realistic than a simple addition, to an image containing the dental arch, of a pre-existing representation of an orthodontic appliance.

The modification of the original image by the neural network may lead to modifications of regions of the original image other than the region of representation of the orthodontic appliance. For example, a careful comparison of FIGS. 3A and 3B will allow it to be seen that the profiles of the lower teeth in the original image (FIG. 3A) and in the modified image (FIG. 3B) are slightly different. These differences, which could be detrimental if the modified image were used for interventions carried out on the teeth (for example to guide a dentist during a milling operation) are not so when the modified image is intended to be presented to the patient. The performance of the neural networks may even make it substantially impossible to detect any differences apart from in the region in which the orthodontic appliance has been represented, as comparison of FIGS. 6A and 6B will show.

A method according to the invention may furthermore comprise one or more of the following optional features:
the modification neural network is trained to:
represent a dental device, and in particular an orthodontic appliance, in a bare-dental-arch image, i.e. in an image not containing the dental device;
delete the representation of a dental device, and in particular of an orthodontic appliance, from an image of an equipped dental arch, i.e. an image containing the dental device; or
replace the representation of a dental device, and in particular of an orthodontic appliance, in an image of an equipped dental arch, with the representation of another dental device, and in particular of another orthodontic appliance, respectively;
the dental device is chosen from an orthodontic appliance, a crown, an implant, a bridge, and a veneer;
the original image is an extra-oral image;
the original image is a photo or a view of a digital three-dimensional model of said arch;
prior to step a), said view is made hyperrealistic by means of a "conversion" neural network;
prior to the acquisition of said view, said model is modified;
said deformation consists in:
a movement of a three-dimensional model of a tooth, and/or
a deformation of a tooth model, and/or
a deletion of a tooth model, and/or
a deformation of a jaw model.
prior to step b), the modification neural network is trained with a historical training database consisting of a set of historical records, each historical record comprising:
a historical image chosen from a photo of a dental scene containing a dental arch not bearing an orthodontic appliance, a view of a dental scene containing a dental arch not bearing an orthodontic appliance, a photo of a dental scene containing a dental arch bearing an orthodontic appliance, and a view of a model representing a dental arch bearing an orthodontic appliance, and
a historical description specifying whether or not the historical image contains an orthodontic appliance,
all orthodontic appliances contained in the historical images being of the same type;
the type of orthodontic appliance includes active multi-bracket appliances or orthodontic retainers or restraints, i.e., for example, all active multi-bracket appliances are considered to be of the same type;

in step c), the modified image is presented on the screen of a telephone of the patient or on a mirror, preferably in augmented reality.

The invention also provides a method for increasing the adherence of a patient to an orthodontic treatment, the method comprising the following steps:

1) choosing a type of orthodontic appliance, for example "active multi-bracket appliance", "orthodontic retainer" or "restraint", and a neural network trained to represent an orthodontic appliance of said type on bare-dental-arch images delivered thereto;
2) simulating, by means of a simulating method according to the invention, the original image acquired in step a) containing a bare dental arch of the patient and the modification neural network being the neural network chosen in step 1);
3) after step c), depending on an opinion of the patient, determining an orthodontic treatment with an orthodontic appliance of the type chosen in step 1) or recommencing in step 1) with another type of orthodontic appliance.

In step 3), the patient gives an opinion on the modified image presented to them in step c). If they are satisfied, the orthodontic treatment is pursued with the orthodontic appliance of the chosen type. Since the orthodontic appliance has been accepted by the patient, their adherence to the treatment is high.

In case of dissatisfaction, a new simulation is started with another type of orthodontic appliance.

Steps b) and c) of a simulating method according to the invention are implemented by a computer, after the original image has been loaded into the computer.

Step 1) and preferably step 3) are also implemented by a computer.

The invention therefore also relates to:
- a computer program comprising program-code instructions for executing these steps b), c), 1) and preferably 3), when said program is executed by a computer,
- a storage medium on which such a program is stored, a memory or a CD-ROM for example.

Definitions

A "patient" is a person for whom a method according to the invention is implemented, regardless of whether this person is undergoing an orthodontic treatment or not.

By "dental care professional" what is meant is any person qualified to provide dental care, this in particular including an orthodontist and a dentist.

A "dental situation" defines a set of characteristics relating to an arch of a patient at a time, for example the position of the teeth, their shape, the position of an orthodontic appliance, etc. at this time.

By "model" what is meant is a digital three-dimensional model. It consists of a set of voxels. A "model of an arch" is a model representing at least one portion of a dental arch and preferably at least 2, preferably at least 3 and preferably at least 4 teeth (FIG. 4 for example).

An observation of a model, under defined observation conditions, in particular from a defined angle and from a defined distance, is called a "view".

An "image" is a two-dimensional representation (formed from pixels) of a scene.

An extra-oral image is an image taken from an observation point outside the mouth, for example taken facing the patient, preferably with a retractor.

A "photo" is a particular image, conventionally a color image, taken with a camera. By "camera" what is meant is any apparatus allowing a photo to be taken, this including a video camera, a cell phone, a tablet or a computer. A view is another example of an image.

A tooth attribute is an attribute the value of which is specific to the teeth. Preferably, a value of a tooth attribute is assigned to each tooth region of the image in question or to each tooth model of a dental-arch model in question. In particular, a tooth attribute does not relate to the image or to the model in its entirety. It derives its value from the characteristics of the tooth to which it relates.

A "scene" consists of a set of elements that may be observed simultaneously. A "dental scene" is a scene containing at least one portion of a dental arch. It contains preferably at least 2, preferably at least 3 and preferably at least 4 teeth.

By "photo of an arch", "view of an arch", "representation of an arch", "scan of an arch", "model of an arch", etc. what is meant is a photo, a view, a representation, a scan or a model, etc. of all or some of said dental arch.

A "training database" is a database of computer records suitable for training a neural network. Each record conventionally comprises an object, for example an image, and information on this object, or its "description". A description contains values of attributes of the object. For example, an attribute of an image of a dental scene may be used to identify a represented type of orthodontic appliance. The attribute is then "Type of orthodontic appliance" and the value of this attribute is, for example "active multi-bracket appliance" or "restraint".

A "local" modification of an original image is a modification that mainly concerns only one portion of this image, the rest of the image not being substantially modified. In fact, the whole original image may be modified, because the image is regenerated. However, to an observer who is not paying special attention, only one portion of the original image will appear to have been modified. For example, the modification may consist in adding the representation of an orthodontic appliance to the original image. Apart from the representation of the orthodontic apparatus, the original image will not appear to have been modified to an observer who does not examine it in detail.

"Dental device" means any device intended to be borne by the dental arch, and in particular an orthodontic appliance, a crown, an implant, a bridge, or a veneer.

In the present description, the qualifiers "original", "modified", "historical", "modification" and "conversion" are used for the sake of clarity.

"Comprising" or "including" or "exhibiting" must be interpreted to be non-limiting, unless otherwise indicated.

BRIEF DESCRIPTION OF THE FIGURES

Other features and advantages of the invention will become apparent on reading the following detailed description and on examining the appended drawing, in which:

FIG. 1 shows, schematically, the various steps of a method according to the invention;

FIGS. 2A and 2B show examples of historical photos used to train the modification neural network;

FIGS. 3A and 3B show an original photo and a photo modified by means of a method according to the invention, respectively;

FIG. 4 shows an example of a model of a dental arch;

FIG. 5 shows a view of a model of a dental arch; and

DETAILED DESCRIPTION

Figure 6A:
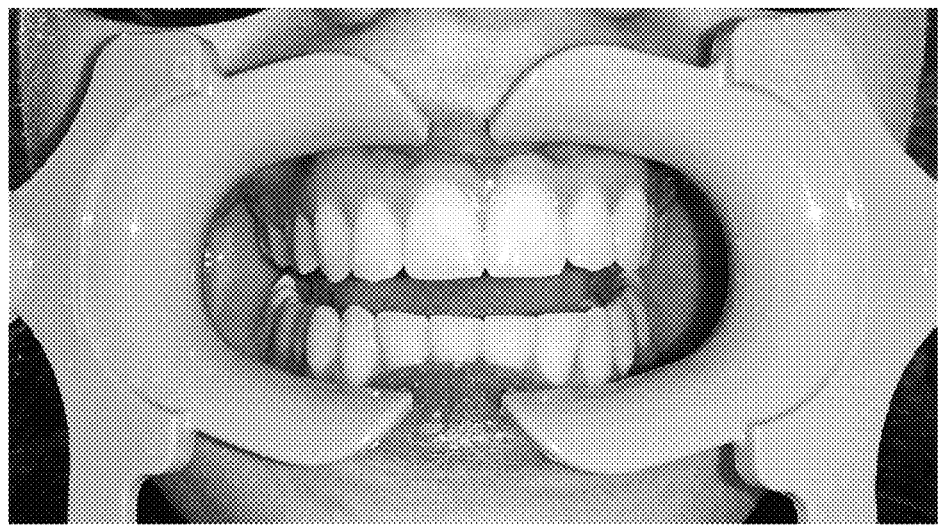
FIGS. 6A and 6B show an original photo and a photo modified by means of a method according to the invention, respectively.
Figure 6B:
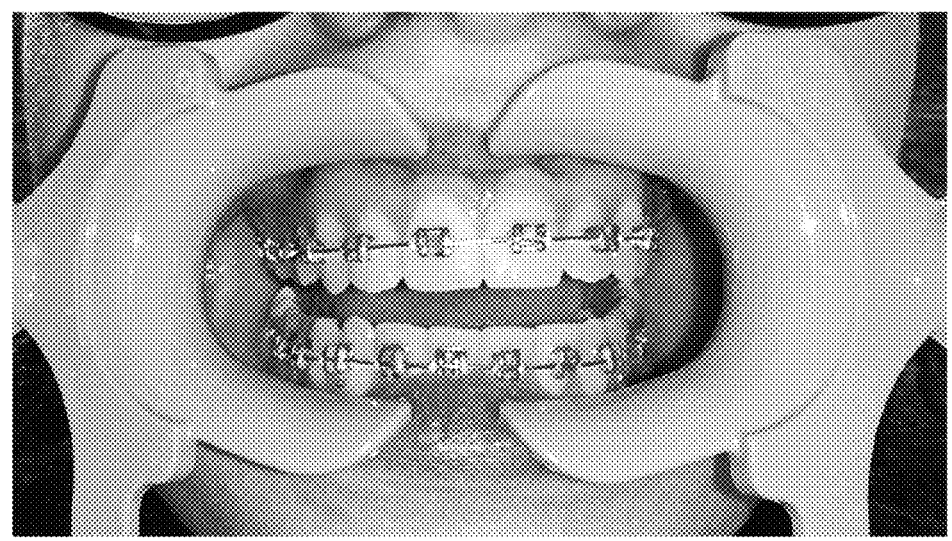

The following detailed description is that of a preferred embodiment, illustrated in FIG. 1, but is non-limiting.

In step a), the original image is preferably an extra-oral image, for example taken facing the patient, preferably with a dental retractor.

The original image may be an "original" photo (FIG. 3).

The original photo is acquired with a camera, preferably chosen from a cell phone, a so-called "connected" camera, a so-called "smartwatch", a tablet or a personal, desktop or portable, computer, comprising a system for acquiring photos. Preferably the camera is a cell phone.

More preferably, during the acquisition of the original photo, the camera is separated from the dental arch by more than 5 cm, more than 8 cm, or even more than 10 cm, this preventing the condensation of water vapor on the lens of the camera and facilitating focusing.

Furthermore, preferably, the camera, in particular the mobile telephone, is not provided with any specific optics for the acquisition of the original photos, this especially being possible due to the separation of the dental arch during the acquisition.

Preferably, an original photo is a color photo and preferably a real-color photo.

Preferably, the original photo is acquired by the patient, preferably without using a holder to immobilize the camera, and especially without a tripod.

The original image may alternatively be a view, called the "original view" (FIG. 5), of a three-dimensional model of the arch, called the "original model".

The original model may be prepared from measurements made on the teeth of the patient or on a cast of their teeth, a plaster cast for example. It is preferably created with a 3D scanner.

The original model is then advantageously very precise.

In one embodiment, the original model is theoretical, i.e. it does not correspond to an actual situation. In particular, the original model may be created by assembling a set of tooth models chosen from a digital library. The arrangement of the tooth models is defined so that the original model is realistic, i.e. so that it corresponds to a situation that could be encountered with a patient. In particular, the tooth models are arranged in an arc, depending on their nature, and oriented realistically. The use of a theoretical original model advantageously allows dental arches to be simulated without having to perform precise measurements on the patient.

The view of the original model used as the original image may be acquired after the original model has been deformed. The deformation thus allows hypothetical dental situations to be simulated.

Preferably, the original model is divided into elementary models, each elementary model representing in 3D one element of the scene modeled by the original model. In particular, it is possible to define, on the basis of the original model, elementary models for each tooth and/or the tongue, and/or the mouth, and/or the lips, and/or the jaws, and/or the gum.

The original model thus divided may then be deformed, for example by moving tooth models, to simulate the effect of an orthodontic treatment or the progress of a relapse, or an aesthetic treatment.

The deformation of the original model may in particular consist in a movement of a tooth model, for example to simulate two teeth separating or two teeth moving closer together, a deformation of a tooth model, for example to simulate bruxism, a deletion of a tooth model, and/or a deformation of a jaw model.

Using a view of an, optionally deformed, original model as the original image decreases the realism of the modified image.

Preferably, the original view is made hyperrealistic before step b), preferably by carrying out the following steps:

i) creating a "conversion" training database consisting of more than 1 000 "conversion" records, each conversion record comprising:

a "conversion" photo containing a dental scene, and a view of a digital three-dimensional "conversion" model modeling said scene, or "conversion view", the conversion view containing said scene just like the conversion photo;

ii) training at least one "conversion" neural network, by means of the conversion training database;

iiiii) subjecting the original view to said at least one trained conversion neural network, so that it makes the original view hyperrealistic.

The conversion neural network may especially be chosen from the list below.

Image-conversion techniques are furthermore described in the article by Zhu, Jun-Yan, et al. "*Unpaired image-to-image translation using cycle-consistent adversarial networks.*"

Trials have shown that the original view thus made hyperrealistic provides substantially the same information as photos, without having to take photos. Specifically, it is very difficult to tell that the hyperrealistic original view is not a photo. A hyperrealistic image may therefore also be qualified "photorealistic".

In step b), the original image resulting from step a) is subjected to a neural network trained to represent the orthodontic appliance in images, or to the "modification neural network".

A "neural network" or "artificial neural network" is a set of algorithms well known to those skilled in the art. The neural network may in particular be chosen from:

networks specializing in image classification (which are called convolutional neural networks (CNNs)), for example AlexNet (2012)

ZF Net (2013)

VGG Net (2014)

GoogleNet (2015)

Microsoft ResNet (2015)

Caffe: BAIR Reference CaffeNet, BAIR AlexNet

Torch: VGG_CNN_S, VGG_CNN_M, VGG_CNN_M_2048, VGG_CNN_M 1024, VGG_CNN_M_128, VGG_CNN_F, VGG ILSVRC-2014 16-layer, VGG ILSVRC-2014 19-layer, Network-in-Network (Imagenet & CIFAR-10)

Google: Inception (V3, V4).

networks specializing in location and detection of objects in an image (object detection networks), for example:

R-CNN (2013)

SSD (Single Shot Multibox Detector: object detection network), faster R-CNN (faster region-based convolutional neural network: object detection network)

faster R-CNN (2015)

SSD (2015).

The above list is not exhaustive.

To be usable, a neural network must be trained by a training method called deep learning.

Such a method is well known.

The modification neural network may in particular be trained using a historical training database consisting of a set of historical records, each historical record comprising:

a historical image chosen from a photo of a dental scene containing a dental arch not bearing an orthodontic appliance (FIG. 2A for example), a view of a dental scene containing a dental arch not bearing an orthodontic appliance, a photo of a dental scene containing a dental arch bearing an orthodontic appliance (FIG. 2B for example), and a view of a model representing a dental arch bearing an orthodontic appliance, and a historical description specifying whether or not the historical image contains an orthodontic appliance and/or identifying, in this image, the representation of the orthodontic appliance.

A historical image consisting of a photo or of a view may be acquired as described above with respect to the acquisition of the original photos and of the original views.

Conventionally, the descriptions are generated by an operator who observes the historical image and completes the description accordingly, by means of a computer. This operation is called labeling.

As the historical records are presented as input to the neural network, the latter gradually learns the difference between an image that contains an orthodontic appliance and an image that does not contain an orthodontic appliance. It thus becomes capable, depending on the original image presented to it, of generating an image modified to contain an orthodontic appliance.

The neural network therefore does not position a view of a 3D model of an orthodontic appliance or a pre-existing image of an orthodontic appliance in the original image.

The network regenerates, on the basis of the original image alone, a complete image incorporating an orthodontic appliance (created from the original image).

The training of the modification neural network also allows it to learn to represent an orthodontic appliance in its context, and in particular under the lighting and/or sharpness conditions of the original image. The incorporation of the orthodontic appliance is thus particularly realistic (FIG. 3B).

The quality of the training of the modification neural network depends directly on the number of historical records in the training database. Conventionally, the historical training database preferably contains more than 10 000 records.

The historical training database preferably contains more than 5 000, preferably more than 10 000, preferably more than 30 000, preferably more than 50 000 and preferably more than 100 000 historical records.

The quality of training of the modification neural network may also be improved if, when the original image is a photo or a view, the historical training database contains only photos or only views, respectively.

The quality of the training of the modification neural network may lastly be improved if the historical training database is specialized for one type of orthodontic appliance. In one preferred embodiment, the neural network is trained with a historical training database in which the historical images that contain an orthodontic appliance contain only orthodontic appliances of a predefined type.

The modification neural network will thus be able to effectively generate an image modified to contain an orthodontic appliance of this type.

In one embodiment, an operator chooses a type of orthodontic appliance to be represented and a computer specializes the training database accordingly, for example such as to retain only historical records the historical images of which do not contain an orthodontic appliance or that contain an orthodontic appliance of the selected type.

In step c), the modified image is presented to the patient, preferably on a computer screen or in augmented reality, for example on a screen of a telephone or on a mirror in which the patient looks at themself.

The patient may thus observe the appearance that they will have when wearing the orthodontic appliance, and therefore more easily accept the corresponding treatment.

Simulation of a Current Dental Situation

In one embodiment, the patient takes the original photo, for example with their cell phone, and a computer, integrated in the cell phone or with which the mobile phone is able to communicate, implements the method. The modified image is presented on the screen of the cell phone.

The patient may thus, without even having to go anywhere, very easily request a simulation of their dental situation based on one or preferably more than one photos of their teeth.

Simulation of a Past or Future Dental Situation

A method according to the invention may also be implemented to generate a modified image representing a simulated dental situation from a digital three-dimensional model of a dental arch. In particular, the dental situation may be simulated at a past or future simulation time, whether within the context of a therapeutic treatment or not.

Preferably, in step a), a hyperrealistic original view is acquired by carrying out the following steps:

a1) at a current time, generating an original model of a dental arch of the patient;

a2) deforming the original model to simulate the effect of time between the current time and a simulation time prior or subsequent to the current time, for example by more than 1 week, 1 month or 6 months;

a3) acquiring an original view of the original model deformed in the previous step;

a4) converting the original view acquired in the previous step into a hyperrealistic original view, preferably by carrying out steps i) to iii).

The modified image thus takes the form of a photo that appears as though it was taken at the simulation time and that contains the orthodontic appliance. It may be presented to the patient in order to show them, for example, their future or past dental situation, and thus motivate them to pursue an orthodontic treatment.

In one embodiment, in step a2), the original model is deformed to simulate the effect of time in the case of poor observance, i.e. if the patient does not comply with medical prescriptions.

Of course, the invention is not limited to the embodiments described above and shown.

In particular, the patient is not limited to a human being. A method according to the invention may be used on another animal.

A training database is not necessarily made up of records of "pairs". In particular, the article by Zhu, Jun-Yan, et al.

"*Unpaired image-to-image translation using cycle-consistent adversarial networks*" describes other possible training databases.

Moreover, the method is not limited to a method for adding the representation of an orthodontic appliance to an image, but may also be used for any modification of the representation of a dental arch, and in particular to delete the representation of an orthodontic appliance in an image of a dental arch bearing an orthodontic appliance or to replace the representation of an orthodontic appliance in an image of a dental arch equipped with an orthodontic appliance with the representation of another orthodontic appliance. The training is adapted accordingly. This adaptation is not particularly difficult.

Lastly, the method is not limited to a method for adding or deleting or modifying a representation of an orthodontic appliance to or in an original image. It extends to the representation of any other dental device.

The invention claimed is:

1. A dental simulating method comprising the following steps:
   a step of subjecting an original image to a neural network, called the "modification neural network", trained to locally modify the original image in order to obtain a "modified image", the original image being a two-dimensional image of a dental arch of a patient and being acquired by a patient with a cellphone, the modified image including a locally modified portion that is generated by the neural network in an artificial way, at the same time as the rest of the modified image;
   the modification neural network being trained to:
      represent a dental device on an image of a dental arch not bearing the dental device; or
      delete the representation of a dental device from an image of a dental arch bearing the dental device; or
      replace the representation of a dental device in an image of a dental arch bearing the dental device, with the representation of another dental device;
      prior to said subjecting step, said modification neural network being trained with a historical training database, consisting of a set of historical records, each historical record comprising:
         a historical image chosen from a photo of a dental scene containing a dental arch not bearing an orthodontic appliance, a view of a dental scene containing a dental arch not bearing an orthodontic appliance, a photo of a dental scene containing a dental arch bearing an orthodontic appliance, and a view of a model representing a dental arch bearing an orthodontic appliance, and
         a historical description specifying whether or not the historical image contains an orthodontic appliance,
      all orthodontic appliances contained in the historical images being of the same type;
   a step of presenting the modified image to the patient.

2. The method as claimed in claim 1, wherein the dental device is chosen from an orthodontic appliance, a crown, an implant, a bridge, and a veneer.

3. The method as claimed in claim 1, wherein the original image is an extra-oral image.

4. The method as claimed in claim 1, wherein the original image is a photo or a view of a digital three-dimensional model of said arch.

5. The method as claimed in claim 4, wherein, prior to acquisition of said original image, said view is made hyper-realistic by means of a "conversion" neural network.

6. The method as claimed in claim 4, wherein, prior to the acquisition of said view, said model is modified.

7. The method as claimed in claim 6, wherein said deformation consists in:
   a movement of a three-dimensional model of a tooth, and/or
   a deformation of a tooth model, and/or
   a deletion of a tooth model, and/or
   a deformation of a jaw model.

8. The method as claimed in claim 1, wherein, prior to said subjecting step, the modification neural network is trained with a historical training database consisting of a set of historical records, to represent an orthodontic appliance on a bare-dental-arch image, each historical record comprising:
   a historical image chosen from a photo of a dental scene containing a dental arch not bearing an orthodontic appliance, a view of a dental scene containing a dental arch not bearing an orthodontic appliance, a photo of a dental scene containing a dental arch bearing an orthodontic appliance, and a view of a model representing a dental arch bearing an orthodontic appliance, and
   a historical description specifying whether or not the historical image contains an orthodontic appliance,
   all orthodontic appliances contained in the historical images being of the same type.

9. The method as claimed in claim 8, wherein the type of orthodontic appliance includes active multi-bracket appliances or orthodontic retainers or restraints.

10. The method as claimed in claim 8, wherein, prior to said subjecting step, an operator chooses a type of orthodontic appliance to be represented and a computer specializes the training database accordingly.

11. The method as claimed in claim 1, wherein, in said presenting step, the modified image is presented in augmented reality.

12. A method for increasing the adherence of a patient to an orthodontic treatment, the method comprising the following steps:
   1) choosing a type of orthodontic appliance and a neural network trained to represent an orthodontic appliance of said type on bare-dental-arch images delivered thereto;
   2) simulating, by means of a simulating method as claimed in claim 1, the acquired original image containing a bare dental arch of the patient and the modification neural network being the neural network chosen in step 1);
   3) after said presenting step, depending on an opinion of the patient, determining an orthodontic treatment with an orthodontic appliance of the type chosen in step 1) or recommencing in step 1) with another type of orthodontic appliance.

13. The method as claimed in claim 1, wherein the modification neural network is trained to:
   add a representation of an orthodontic appliance to the original image, or
   make any modification of the representation of the dental arch.

14. The method as claimed in claim 1, wherein, at said presenting step, the modified image is presented on the screen of the cellphone or on a mirror.

* * * * *